US008043273B2

(12) United States Patent
Van Gompel et al.

(10) Patent No.: US 8,043,273 B2
(45) Date of Patent: Oct. 25, 2011

(54) DISPOSABLE UNDERGARMENT WITH A STRETCHABLE ABSORBENT INSERT AND METHOD FOR THE USE THEREOF

(75) Inventors: Paul T. Van Gompel, Hortonville, WI (US); Yung H. Huang, Appleton, WI (US); Russell E. Thorson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2823 days.

(21) Appl. No.: 10/325,500

(22) Filed: Dec. 19, 2002

(65) Prior Publication Data

US 2004/0122405 A1     Jun. 24, 2004

(51) Int. Cl.
*A61F 13/15* (2006.01)
(52) U.S. Cl. ................. 604/385.22; 604/385.23
(58) Field of Classification Search ............. 604/385.22, 604/385.23
See application file for complete search history.

(56) References Cited

U.S. PATENT DOCUMENTS

| | | |
|---|---|---|
| 3,488,778 A | 1/1970 | Goujon et al. |
| 3,828,367 A | 8/1974 | Bourgeois |
| 4,302,853 A | 12/1981 | Mesek |
| 4,515,595 A | 5/1985 | Kievit et al. |
| 4,595,441 A | 6/1986 | Holvoet et al. |
| 4,612,674 A | 9/1986 | Hashimoto |
| 4,652,487 A | 3/1987 | Morman |
| 4,655,760 A | 4/1987 | Morman et al. |
| 4,657,802 A | 4/1987 | Morman |
| 4,663,106 A | 5/1987 | Pomplun et al. |
| 4,663,220 A | 5/1987 | Wisneski et al. |
| 4,707,398 A | 11/1987 | Boggs |
| 4,720,415 A | 1/1988 | Vander Wielen et al. |
| 4,724,184 A | 2/1988 | Killian et al. |
| 4,726,807 A | 2/1988 | Young |
| 4,756,709 A | 7/1988 | Stevens |
| 4,760,764 A | 8/1988 | De Jonckheere et al. |
| 4,781,966 A | 11/1988 | Taylor |
| 4,789,699 A | 12/1988 | Kieffer et al. |
| 4,808,176 A | 2/1989 | Kielpikowski |

(Continued)

FOREIGN PATENT DOCUMENTS

EP      0 449 271 A1     10/1991

(Continued)

OTHER PUBLICATIONS

Patent Application entitled, "Body Conforming Absorbent Garment and Methods for the Use and Manufacture Thereof", U.S. Appl. No. 10/274,503, filed Oct. 18, 2002.

(Continued)

*Primary Examiner* — Melanie Hand
*Assistant Examiner* — Ginger T Chapman
(74) *Attorney, Agent, or Firm* — H. Michael Kubicki (57) ABSTRACT

A disposable undergarment includes a body panel and an absorbent insert having a back sheet connected to a top sheet and a retention portion disposed between the back sheet and the top sheet. At least one of the back sheet and the top sheet is stretchable and includes an elastic material. At least one of the back sheet and the top sheet is connected to the body panel. A method of using a disposable undergarment includes stretching at least one of the back sheet and the top sheet. A method of instructing a user on the use of the disposable undergarment is also provided.

19 Claims, 4 Drawing Sheets

U.S. PATENT DOCUMENTS

| | | | |
|---|---|---|---|
| 4,834,738 A | 5/1989 | Kielpikowski | |
| 4,863,779 A | 9/1989 | Daponte | |
| 4,965,122 A | 10/1990 | Morman | |
| 4,981,747 A | 1/1991 | Morman | |
| 5,114,781 A | 5/1992 | Morman | |
| 5,116,662 A | 5/1992 | Morman | |
| 5,151,092 A | 9/1992 | Buell et al. | |
| 5,169,706 A | 12/1992 | Collier, IV et al. | |
| 5,171,236 A | 12/1992 | Dreier et al. | |
| 5,171,239 A * | 12/1992 | Igaue et al. | 604/385.29 |
| 5,226,992 A | 7/1993 | Morman | |
| 5,260,126 A | 11/1993 | Collier, IV et al. | |
| 5,288,791 A | 2/1994 | Collier, IV et al. | |
| 5,330,598 A | 7/1994 | Erdman et al. | |
| 5,336,545 A | 8/1994 | Morman | |
| 5,366,793 A | 11/1994 | Fitts, Jr. et al. | |
| 5,385,775 A | 1/1995 | Wright | |
| 5,399,219 A | 3/1995 | Roessler et al. | |
| 5,414,470 A | 5/1995 | Hotta et al. | |
| 5,496,429 A | 3/1996 | Hasse et al. | |
| 5,503,908 A | 4/1996 | Faass | |
| 5,569,234 A | 10/1996 | Buell et al. | |
| 5,575,783 A * | 11/1996 | Clear et al. | 604/385.22 |
| 5,593,400 A | 1/1997 | O'Leary | |
| 5,599,417 A | 2/1997 | Glaug et al. | |
| 5,611,790 A | 3/1997 | Osborn, III et al. | |
| 5,695,846 A | 12/1997 | Lange et al. | |
| 5,716,351 A | 2/1998 | Roe et al. | |
| 5,746,730 A | 5/1998 | Suzuki et al. | |
| 5,782,819 A | 7/1998 | Tanzer et al. | |
| 5,807,368 A | 9/1998 | Helmer | |
| 5,817,086 A | 10/1998 | Kling | |
| 5,827,259 A | 10/1998 | Laux et al. | |
| 5,846,232 A | 12/1998 | Serbiak et al. | |
| 5,858,151 A | 1/1999 | Igaue et al. | |
| 5,932,497 A | 8/1999 | Morman et al. | |
| 5,947,948 A | 9/1999 | Roe et al. | |
| 6,015,935 A | 1/2000 | LaVon et al. | |
| 6,049,023 A | 4/2000 | Blenke et al. | |
| 6,099,516 A | 8/2000 | Pozniak et al. | |
| 6,113,717 A | 9/2000 | Vogt et al. | |
| 6,120,487 A | 9/2000 | Ashton | |
| 6,132,410 A | 10/2000 | Van Gompel | |
| 6,149,637 A | 11/2000 | Allen et al. | |
| 6,171,432 B1 | 1/2001 | Brisebois et al. | |
| 6,187,425 B1 | 2/2001 | Bell et al. | |
| 6,217,563 B1 * | 4/2001 | Van Gompel et al. | 604/385.101 |
| 6,217,692 B1 | 4/2001 | Kling | |
| 6,258,077 B1 | 7/2001 | Buell et al. | |
| 6,264,641 B1 | 7/2001 | Van Gompel et al. | |
| 6,264,643 B1 | 7/2001 | Toyoda | |
| 6,264,784 B1 | 7/2001 | Menard et al. | |
| 6,302,871 B1 | 10/2001 | Nakao et al. | |
| 6,306,122 B1 | 10/2001 | Narawa et al. | |
| 6,323,389 B1 | 11/2001 | Thomas et al. | |
| 6,325,787 B1 | 12/2001 | Roe et al. | |
| 6,336,922 B1 | 1/2002 | VanGompel et al. | |
| 6,352,528 B1 | 3/2002 | Weber et al. | |
| 6,359,192 B1 | 3/2002 | Schmidt et al. | |
| 6,364,863 B1 | 4/2002 | Yamamoto et al. | |
| 6,367,089 B2 | 4/2002 | Van Gompel et al. | |
| 6,375,646 B1 | 4/2002 | Widlund et al. | |
| 6,387,471 B1 | 5/2002 | Taylor et al. | |
| 7,314,465 B2 * | 1/2008 | Van Gompel et al. | 604/395 |
| 2001/0025164 A1 | 9/2001 | Krautkramer et al. | |
| 2001/0025165 A1 | 9/2001 | Shimoe | |
| 2001/0047159 A1 | 11/2001 | Mizutani | |
| 2002/0002021 A1 | 1/2002 | May et al. | |
| 2002/0009940 A1 | 1/2002 | May et al. | |
| 2002/0010450 A1 | 1/2002 | Suzuki et al. | |
| 2002/0104608 A1 | 8/2002 | Welch et al. | |

FOREIGN PATENT DOCUMENTS

| | | |
|---|---|---|
| EP | 0 753 292 A2 | 1/1997 |
| EP | 0 907 510 B1 | 4/1999 |
| EP | 0 794 751 B1 | 6/1999 |
| EP | 1 108 372 A1 | 6/2001 |
| EP | 1 240 881 A2 | 9/2002 |
| EP | 1 249 214 A | 10/2002 |
| EP | 1 366 735 A1 | 12/2003 |
| EP | 1 428 487 A1 | 6/2004 |
| EP | A-1- 574 193 A | 9/2005 |
| FR | 2644694 | 9/1990 |
| GB | 2242348 A * | 10/1991 |
| JP | 03176053 A | 7/1981 |
| WO | WO 93/17648 | 9/1993 |
| WO | WO 98/29251 | 7/1998 |
| WO | WO 99/56688 A1 | 11/1999 |
| WO | WO 00/39201 | 6/2000 |
| WO | WO 01/87588 A2 | 11/2001 |
| WO | WO 01/87589 A2 | 11/2001 |
| WO | WO 01/88245 A2 | 11/2001 |
| WO | WO 02/24131 A1 | 3/2002 |
| WO | WO 2004/030477 A | 4/2004 |
| WO | WO 2004/060238 A | 7/2004 |

OTHER PUBLICATIONS

International Search Report in corresponding International Application No. PCT/US03/28637, dated Jan. 22, 2004, 9 pages.

Patent Application entitled, "Three-Piece Disposable Undergarment and Method for the Manufacture Thereof", U.S. Appl. No. 10/261,805, filed Oct. 1, 2002.

International Search Report in corresponding International Application No. PCT/US03/28245, dated Feb. 18, 2004, 7 pages.

International Search Report in corresponding International Application No. PCT/US03/39405, dated Apr. 16, 2004, 6 pages.

International Search Report in International Application No. PCT/US2004/008429, dated Aug. 17, 2004, 7 pages.

International Preliminary Report on Patentability in International Application No. PCT/US2004-008429, dated Aug. 17, 2004, 3 pages/

Examination report in EP Patent Application No. EPO 03 796 949.0 dated Dec. 23, 2005, 9 pages.

\* cited by examiner

DISPOSABLE UNDERGARMENT WITH A STRETCHABLE ABSORBENT INSERT AND METHOD FOR THE USE THEREOF

BACKGROUND

The present invention relates generally to disposable undergarments, and in particular, to an undergarment having a stretchable absorbent insert, and to the method for the use thereof.

Disposable undergarments can be configured in many different forms. For example, disposable absorbent garments can be configured as a pant-type, pull-on garment, or as a diaper-type product that is drawn up between the legs and fastened about the waist with various fastening systems. In some configurations, the garment is formed from an absorbent insert attached to a body panel, which may be stretchable and elongatable. Often, the absorbent insert is secured across the entire width of the portion of the absorbent insert that overlaps the body panel. As such, the absorbent insert, which typically is not stretchable, can reduce or otherwise impede the elongation of the body panel, thereby adversely affecting its ability to conform to the body of the user.

Therefore the need remains for an improved undergarment that conforms to the body of the user during use without interference from the absorbent insert.

SUMMARY

Briefly stated, in one embodiment, a disposable undergarment includes a body panel and an absorbent insert having a back sheet connected to a top sheet and a retention portion disposed between the back sheet and the top sheet. At least one of the back sheet and the top sheet is stretchable and includes an elastic material. At least one of the back sheet and the top sheet is connected to the body panel.

In another aspect, a method of using a disposable undergarment includes stretching at least one of the back sheet and the top sheet. In yet another aspect, a method of instructing a user on the use of the disposable undergarment is also provided.

The various embodiments described herein provide significant advantages over other disposable undergarments, and methods for the use thereof. For example, the absorbent insert can be stretched with the body panel to conform to the body of the user, and thereby provide a snug fit to the body of the user. In addition, an elastic component of the absorbent insert, e.g., the back sheet, allows the absorbent insert, and in particular the back sheet, to stretch and retract, further improving the fit of the garment.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

Many of the features and dimensions portrayed in the drawings, and in particular the presentation of layer thicknesses and the like, and the spacing therebetween, have been somewhat exaggerated for the sake of illustration and clarity.

DETAILED DESCRIPTION OF THE PRESENTLY PREFERRED EMBODIMENTS

It should be understood that the term "longitudinal," as used herein, means of or relating to length or the lengthwise direction 500. The term "laterally," as used herein, means situated on, directed toward or running from side to side. The term "first direction" generally refers to a path, line or course rather than a vector, and includes and applies equally to opposite orientations along the path, line or course, including for example and without limitation movement along a path, line or course in both directions (as indicated by the bi-directional arrows associated with the longitudinal and lateral directions 500, 502). Likewise, the term "second direction" generally refers to a path, line or course rather than a vector (not orientation dependent), and includes for example and without limitation movement along a path, line or course in both directions. In one example, the first direction is defined by and refers to one of the longitudinal and lateral directions, while the second direction refers to the other of the longitudinal and lateral directions.

The term "bodyside" should not be interpreted to mean in contact with the body of the user, but rather simply means the side that would face toward the body of the user, regardless of whether an undergarment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the undergarment is actually being worn by a user, regardless of whether any such outer garments are actually worn and regardless of whether there may be intervening layers between the component and any outer garment.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected, during the normal operation and use of the absorbent garment.

The terms "connecting," "coupled," "attached," and "secured," and variations thereof, broadly covers two or more items being directly connected one to the other, or by way of one or more intervening members or components.

Referring to FIGS. 6-9, an undergarment 2 has a body chassis member 8 that includes a first, front body panel 4 and a second, rear body panel 6. The terms "body chassis member" and "body panel" refer to the portion(s) of the undergarment, whether made of one or more layers or substrates or of one or more pieces or components, that is/are fitted circumferentially around the body of the user, for example about the waist region of the user, and/or one or more of the user's lower back, buttock, hips, crotch and abdomen.

The first and second body panels each have an inner, bodyside surface 10 and an outer, garment side surface 12. The first, front body panel 4 has a first terminal edge 14 formed along the crotch region of the garment and a second terminal edge 20 formed along the waist region of the garment. In one embodiment, the second first and second terminal edges are linear but can assume other shapes. Likewise, the second, rear body panel 6 has a first terminal edge 22 formed along the crotch region of the garment and a second terminal edge 28 that is formed along the waist region of the garment. In one embodiment, the first and second terminal edges are linear but can assume other shapes. Each of the first and second body panels have an outboard side edge 30, 32 formed along the outer periphery of the opposite side portions of the first and second body panel. In one embodiment, the side edges 30, 32 are the same length, although it should be understood that the outboard side edges of the front and rear body panels could have different lengths relative to each other. In one embodiment, a tapered edge 18, 26 connects the terminal edges 14, 22 with the side edges 30, 32 respectively and defines a portion of a leg opening 34. Alternatively, the terminal edges and the tapered edges can be formed as a curvilinear edge, for example and without limitation in a sinusoidal pattern. In yet another embodiment, the terminal edges are linear and extend across the entire lateral width of the garment without any tapered edges. In one embodiment, the terminal edges 14, 22 of the first and second body panels are spaced apart in the crotch region so as to form a gap or space 34 therebetween.

In an alternative embodiment, shown in FIGS. 1-5, the body chassis member 108, or outer cover, extends substantially the entire length of the garment and defines and integrally forms the first, front body panel 104 and the second, rear body panel 106, as well as a crotch portion 124 extending therebetween. In this embodiment, with the front and rear body panels 104, 106 integrally formed with a crotch portion 124, the body panels have tapered edges 118, 126 that form portions of the leg opening, side edges 130, 132 and opposite terminal edges 120, 128.

Figure 1:
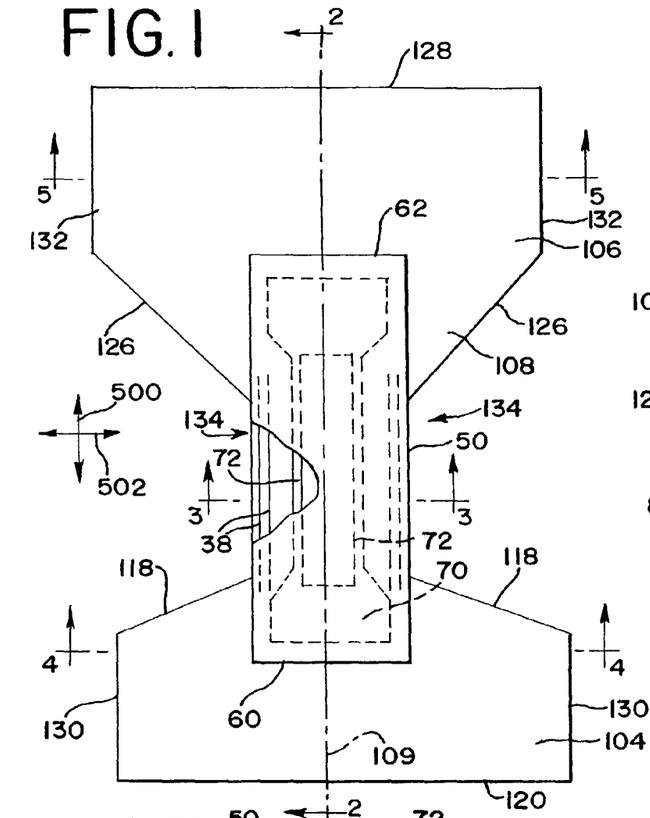
FIG. 1 is a plan view of a first embodiment of a disposable undergarment taken from the bodyside thereof.
Figure 2:
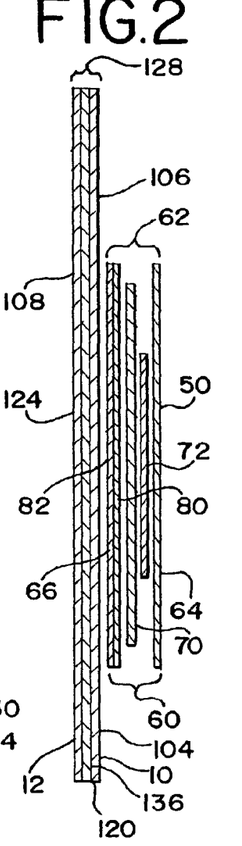
FIG. 2 is a schematic illustration of a cross-sectional view of the disposable undergarment taken along line 2-2 in FIG. 1.
Figures 6, 7:
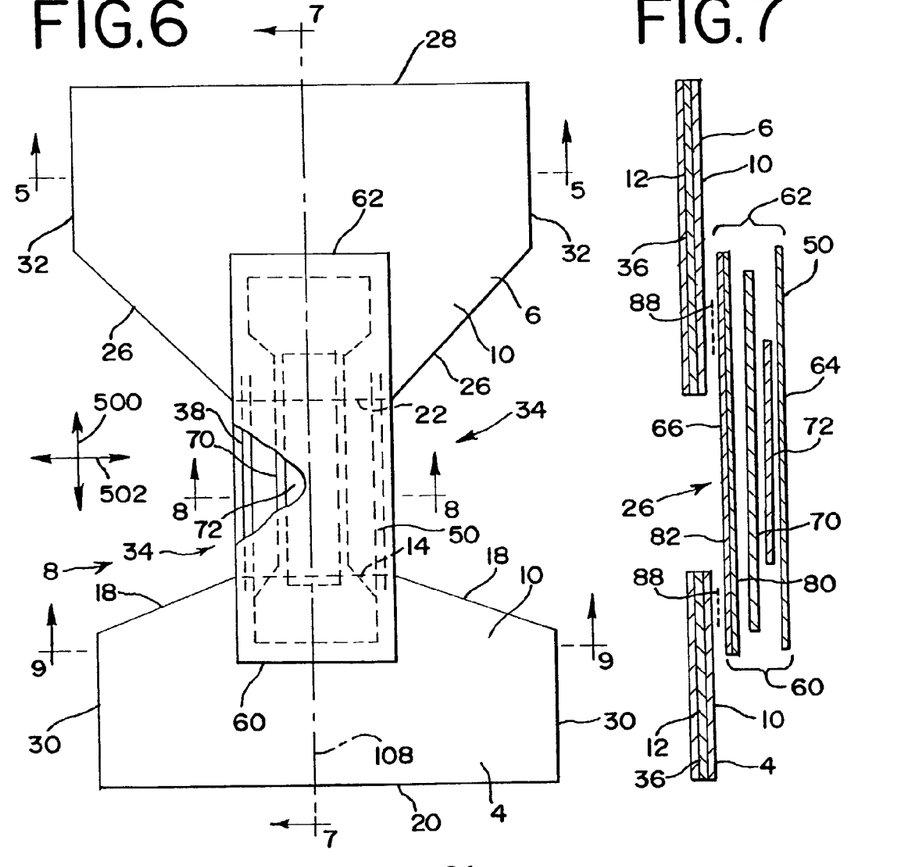
FIG. 6 is a plan view of a second embodiment of a disposable undergarment taken from the bodyside thereof.
FIG. 7 is a schematic illustration of a cross-sectional view of the disposable undergarment taken along line 7-7 in FIG. 6.
Figure 8:
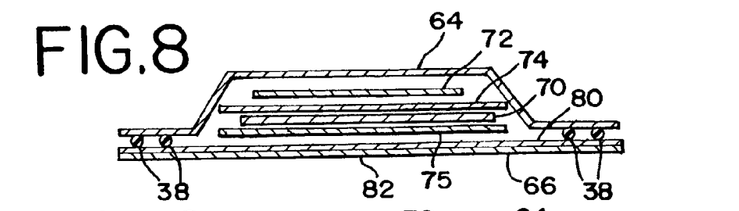
FIG. 8 is a schematic illustration of a cross-sectional view of the disposable undergarment taken along line 8-8 in FIG. 6.

Referring to FIGS. 2 and 7, one or more, and in one embodiment a plurality, meaning two or more, elastic elements are secured to each of the first and second body panels 4, 6, 104, 106. In one embodiment, a plurality of elastic elements are spaced across substantially the entire waist portion of the front and rear body panel, although they may be spaced across a lesser length. For example, elastic elements can extend along the upper waist portion and along the lower terminal edge defining in part a leg opening.

In one embodiment, the front body panel has a "non-elasticized" area wherein there are no elastic elements, or other elastic or elastomeric backing members, incorporated therein or making up any portion of the thickness or cross-section of the body panel at that area. It should be understood, that in various embodiments; one or more separate waist bands, with or without elastic elements, can be secured to one or both of the rear and front body panels, preferably along the upper terminal edges 20, 28, 120, 128 thereof. Likewise, one or more separate leg bands can be secured to one or both of the rear and front body panels along the edge 18, 26, 118, 126 of the body panel and/or along the edge of the crotch portion forming and defining the leg openings 34, 134. Alternatively, one or both of the body panels can be formed without any elastic elements.

The various waist and leg elastic elements can be formed from rubber or other elastomeric materials. One suitable material is a LYCRA® elastic material. For example, the various elastic elements can be formed of LYCRA® XA Spandex 540, 740 or 940 decitex T-127 or T-128 elastics available from E.I. duPont De Nemours and Company, having an office in Wilmington, Del.

Referring to FIGS. 2-5 and 7-9, each body panel 4, 6, 104, 106 is preferably formed as a composite, or laminate material, otherwise referred to as substrates or laminates, with an elastic core 36, 136 sandwiched therebetween. In one embodiment, the elastic core 36, 136 is made of an elastomeric film or nonwoven elastic or stretchable material including for example block copolymers of polystyrene, polyisoprene or polybutadiene, copolymers of ethylene, natural rubbers, urethanes, kratons, and co-extrusions/blends of the aforementioned material The elastic core can be formed as a membrane or from a plurality of elastic strands, as described above. In one embodiment, two or more layers 40, 140, 164, 166 are bonded to the elastic core 36, and/or each other, with various adhesives, such as hot melt, or by other techniques, including for example and without limitation ultrasonic bonding and heat pressure sealing. In one embodiment, the two layers are made of a non-woven material such as a spunbond material, a bonded carded material or other known materials. In this way, the body panels are made of a stretchable/elastic material.

As used herein, the interchangeable terms "stretchable" and "elastic," and variations thereof, refer to a material that can elongate or deform (stretch) in response to the application of a tensile force under certain test conditions herein defined below, and upon removal of the tensile force have a length that is less than about 128% of the original length, which corresponds to hysteresis of less than about 28%. Thus, a stretchable or elastic material can be stretched and upon relaxing the material, will tend to resume its original shape. As used herein, "extensible" materials are those materials having a length of greater than about 128% of the original length when elongated and relaxed under certain test conditions herein defined below, which corresponds to a hysteresis of greater than about 28%.

It should be understood that the body panels can be made of a single layer or substrate of non-woven material, a bi-layer substrate made of non-woven materials without an elastic core, or more than two layers or substrates. Of course, it should be understood that other knitted or woven fabrics, non-woven fabrics, elastomeric materials, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric.

In one embodiment, the body panel material can be secured to the elastic core, such as an elastomeric layer or elastic strands or ribbons, which have been elongated and retracted, such that the material is gathered when the elastic element(s) are relaxed. Alternatively, the material can be gathered and laminated to non-elongated elastic elements. In one preferred embodiment, the body panel includes a gathered elastic laminate made from nonwoven base sheets bonded with elongated elastic elements sandwiched therebetween.

In various preferred embodiments, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels can include an elastomeric material that is elastomerically stretchable at least along one or both of the lateral article width and the longitudinal article length. Examples of such elastomeric composite materials can include a continuous filament stretch bonded laminate (CFSBL), a vertical filament laminate (VFL), neck-bonded-laminate (NBL), a stretch-bonded-laminate (SBL), a necked-stretch bonded laminate (NSBL) or a necked-thermal laminate, or the like, as well as combinations thereof. Exemplary CFSBL, NBL, SBL, and NSBL materials are described in U.S. Pat. Nos. 5,226,992, 4,981,747, 4,965,122, 5,336,545, 5,385,775, 5,414,470, 4,720,415, 4,789,699, 4,781,966, 4,657,802, 4,652,487, 4,655,760, 5,116,662 and 5,114,781, and 6,323,389, all of which are hereby incorporated herein by reference. Exemplary VFL materials are described in U.S. Provisional Patent Application Ser. No. 60/204,307, filed May 15, 2000 and entitled "Method and Apparatus for Producing Laminated Articles," and PCT application WO 01/88245 A2, both assigned to Kimberly-Clark Worldwide, Inc., the Assignee of the present application, with the entire disclosures of both being hereby incorporated herein by reference. Such laminates can provide an improved combination of cloth-like feel and elastomeric stretchability. The body panels can be composed of materials that are elastic or elastomeric and exhibit biaxial stretch characteristics or lateral/longitudinal stretch characteristics, or which are extensible composites. Additional waist and leg elastic elements can be added to, but are not necessarily required by, the body panels.

In one embodiment, the body panel material is extensible but not elasticized. For example, the body panel can be made of a film or non-woven that is attached, by way of adhesives or thermal bonding, to an extensible non-woven material. Alternatively, the body panel can be made of a low modulus film such as Ethylene Methyl acrylate (EMA).

As shown in the embodiments of FIGS. 1-7 and 9, the entirety of the body panels 4, 6, 104, 106, and the crotch portion 124 of chassis 108, are elasticized, such that the entirety of each of the body panels can elongate and conform to the body of the user without any substantial spacing between the body panel and the user's body, and without the attendant bulkiness of a non-elasticized material.

In one embodiment, the body panels are breathable, cloth-like, multi-directional nonwoven laminates with stretch or extensible properties. In one embodiment, the non-woven layers are pre-necked, for example between about 10% and about 80%, in the longitudinal direction, which provides extensibility in the longitudinal direction with minimal force.

In one embodiment, the body chassis member 8, 108 are made of non-woven laminates of two layers of longitudinally extensible 0.60 osy polypropylene spunbond material with elongated strands of Lycra® elastic sandwiched between the spunbond layers and thereafter adhesively bonded. In particular, the body panel material is necked in the cross direction. As used herein, the term "necked," and variations thereof, refers to any material that has been constricted in at least one dimension by applying a tensioning force in a direction that is perpendicular to the desired direction of neck-down. Processes that may be used to constrict a material in such a manner include, for example and without limitation, drawing processes. The elastics are then elongated in the machine direction and secured to the body panel material. The elastics are then allowed to retract so as to gather the necked spunbond material in the lateral (machine) direction thereby creating an elastically gathered non-woven body panel with longitudinal extensibility. The term "gather," and variations thereof, as used herein means puckered, or contracted into folds or wrinkles, which should be understood as including micropleats.

In this way, the body panel can be elongated in both the longitudinal and lateral direction to conform to the body of the user when the garment is applied thereto. In particular, as the user pulls the garment up over their hips, the non-woven laminate body panels stretch in the lateral direction while the leg regions of the front and rear body panels conform to the crotch and body lines of the user. At the same time, the body panel material extends in the longitudinal direction to conform to the buttocks and stomach of the user. The extensibility of the body panels follows the natural curvature of user's body to provide conformance thereto. As the body panel extends in the longitudinal direction, the spacing between the laterally extending elastic elements, incorporated in one embodiment, will increase.

The body chassis non-woven material is preferably substantially hydrophobic, which may optionally be treated with a surfactant or otherwise processed to impart a desired level of wettability and hydrophilicity. In one particular embodiment of the invention, the body panel is a nonwoven, wire-weave spunbond polypropylene fabric composed of about 1.6 denier fibers formed into a web having a basis weight of about 0.6 osy. One suitable non-woven material is the Corinth 0.60 osy, 1.6 dpf wireweave, nonwettable Metallocene (EXXON ACHIEVE 2854 PP) spunbond material manufactured by Kimberly-Clark Corporation, the assignee of the present application.

The crotch portion of the various undergarments connecting the front and rear body panels 4, 6, 104, 106, whether integrally formed or separately connected with an absorbent insert, can be folded such that the side edges 30, 32, 130, 132 of the front and rear body panels 4, 6, 104, 106 are aligned, whereinafter they can be fixedly secured at a seam to form the leg opening 34, 134. The seam can be formed by bonding, sewing or otherwise attaching the side edges. Alternatively, the product can remain "open," wherein the body panels are releasably secured with one or more fastening members as explained below.

In one embodiment, the garment includes a combination of side edges that are secured to form a seam and fastening members that allow the fit of the undergarment to be adjusted. For example, in one embodiment, fastening members are preferably attached to the front body panel and extend inboard relative to the outboard side edge of the front body panel from an attachment location, which is preferably spaced inboard from the side edge. A landing member can be formed on or secured to the body panel to receive a refastenable portion of the fastening member. One or more lines of weakness can be provided along the front or rear body panel such that one or both of the body panels are breakable. The lines of weakness can comprise a perforation or other series of cuts, a thinning, breakage or separation of material, or a strip of a different kind of material bridging portions of the body panel that is more easily torn or broken than the other material thereof, which allow a user or the manufacturer to separate portions of the body panel. For example, the undergarment can be broken along the lines of weakness after the garment is applied to a user, or beforehand. IN one embodiment, the fastening members are secured to the garment-side surface of the body panel.

It should be understood that, in other embodiments, the fastening members can be secured to the rear body panel and engage the front body panel or, conversely, can be secured to the front body panel and engage the rear body panel, preferably along at least a portion that is not elasticized. In one embodiment, the fastening members are fixedly secured to the outer, garment-side surface of the front and/or rear body panels, and releasably engage the outer, garment-side surface of the front and/or rear body panels, although it should be understood that the fastening members could be fixedly secured to an inner body-side surface of front and/or rear body panels and releasably engage an inner, body-side surface of the front and/or rear body panels.

When incorporated into a disposable absorbent undergarment, the fastening members can include a refastenable portion, such as an array of hook members, adhesives, such as pressure sensitive adhesives, buttons, zippers, snaps and other releasable and reattachable fastening devices. In various embodiments, the fastening member includes one, two or more than two tab members. In one embodiment, the fastening members comprise a carrier member, which is preferably fixedly secured to the side portions of the front body panel with adhesive bonds, sonic bonds, thermal bonds, pinning, stitching or other known types of attachment. In alternative embodiments, the fastening members can be fixedly secured to the rear body panel or to one or both of the front and rear body panels, for example, at the seam, as explained above.

Figure 3:
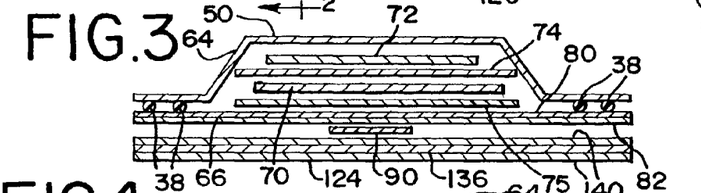
FIG. 3 is a schematic illustration of a cross-sectional view of the disposable undergarment taken along line 3-3 in FIG. 1.
Figure 4:
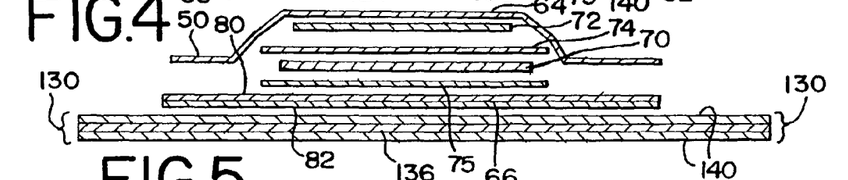
FIG. 4 is a schematic illustration of a cross-sectional view of the disposable undergarment taken along line 4-4 in FIG. 1.
Figure 5:
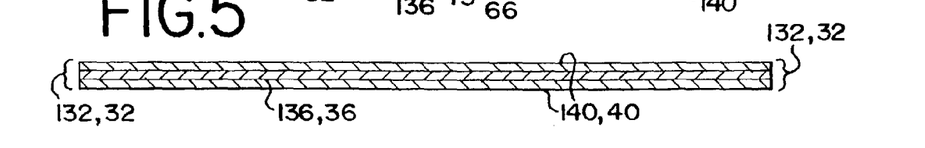
FIG. 5 is a schematic illustration of a cross-sectional view of the disposable undergarment taken along line 5-5 in FIGS. 1 and 6.
Figure 9:
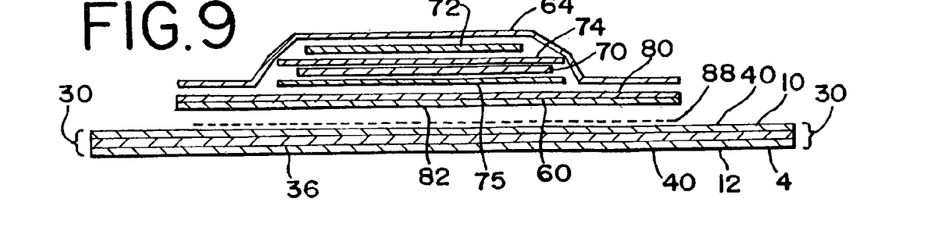
FIG. 9 is a schematic illustration of a cross-sectional view of the disposable undergarment taken along line 9-9 in FIG. 6.

Referring to the embodiments of FIGS. 1-9, an absorbent insert 50 is formed as a separate subassembly connected to a bodyside surface of the body chassis member 8, 108 (whether formed as a single integral member having a front and rear body panel and a crotch portion as shown in FIGS. 1-5, or as discrete and spaced apart front and rear body panel members as shown in FIGS. 6-9). In either embodiment, the absorbent insert 50 has first and second opposed terminal end edges 60, 62. In the embodiment of FIGS. 6, 7 and 9, the absorbent insert 50 bridges the gap between the terminal edges 14, 22 of the body panels 4, 6 and is connected respectively to those body panels at attachment locations 88. The absorbent insert 50 that overlap the body panels or body chassis member can be minimally attached thereto with an attachment having a width of between about 10% and about 100% of the width of the absorbent insert. Therefore, in various embodiments, as shown in FIG. 3, the side edges of the absorbent insert are not attached to the body panels or body chassis.

In one embodiment, shown in FIGS. 3, 4, 8 and 9, the absorbent insert 50 includes a substantially liquid permeable top sheet 64, or liner, and a substantially liquid impermeable back sheet 66. A retention portion 70 is disposed or sandwiched between the topsheet and the backsheet, which are connected.

Referring to FIGS. 1-9, the top sheet 64, back sheet 66 and other components of the absorbent insert can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein.

In one embodiment, one or more crotch elastic members 38 are sandwiched between the top sheet 64 and backsheet 66 along the side edges thereof. The elastic members 38 can extend the entire longitudinal extent of the absorbent insert, or along only a portion thereof.

Additional layers, including for example, a liquid acquisition and distribution layer 72, also referred to as a surge or transfer layer, are also preferably incorporated into the absorbent insert. In one embodiment, the transfer layer does not run the entire length of the absorbent insert and is shorter than the retention portion.

In one embodiment, the retention portion 70, transfer layer 72 and other components, such as tissue layers, are free floating (unattached) between the back sheet 64 and the top sheet 66, which are secured along only the peripheral edges thereof. Alternatively, the retention portion 70, transfer layer 72 and other components are minimally attached to one or both of the back sheet 66 and top sheet 64. For example, the retention portion can be secured to the back sheet along an attachment location positioned along the longitudinal centerline 108 of the retention portion. Alternatively, or in combination with the back sheet connection, the transfer layer or retention portion can be minimally attached to the top sheet. In this way, the retention portion 70, transfer layer 72 and other components do not impede or substantially affect the lateral stretchability and extensibility of the absorbent insert 50 and in particular the top sheet and back sheet, at least one of which is secured to the body chassis.

In another alternative embodiment (not shown), the retention portion is secured along the centerline at a point midway between the two ends of the retention portion. In this embodiment, the retention portion also does not restrict or impede the stretchability and extensibility of the absorbent insert, and in particular the top sheet and back sheet, in the lateral or longitudinal directions 500, 502.

In other embodiments, the top sheet is indirectly joined to the backsheet by affixing the topsheet to intermediate layers, such as the surge layer or retention portion, which in turn is affixed to the backsheet. The absorbent insert also may include barrier cuffs, or leakage control shields, formed along the opposite longitudinally extending edges of the absorbent composite.

In one embodiment, the back sheet 66 is a stretchable, elastic, liquid impervious member. Alternatively, the back sheet may be liquid permeable, e.g., when an additional barrier layer is used with the retention portion. In one embodiment, shown in FIGS. 2-5 and 7-9, the back sheet 66 is a-laminate structure made of a stretchable, elastic material, such as an elastomeric film 80, which is laminated to an extensible non-woven material layer 82. It should be understood that the backsheet can be formed from a single layer or substrate or more than two layers or substrates.

The backsheet 66 prevents various bodily fluids and exudates from wetting or otherwise contaminating various bedding or outer garments worn by the user over the absorbent garment. The backsheet can be made of the same materials described above in connection with the body panels. In one embodiment, the backsheet can include a film, which can be made of the various materials described above.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various embodiments, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

In one example, the backsheet can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

Three types of backsheet materials were tested for stretchability/extensibility.

Example 1

VFL Material

Figure 10:
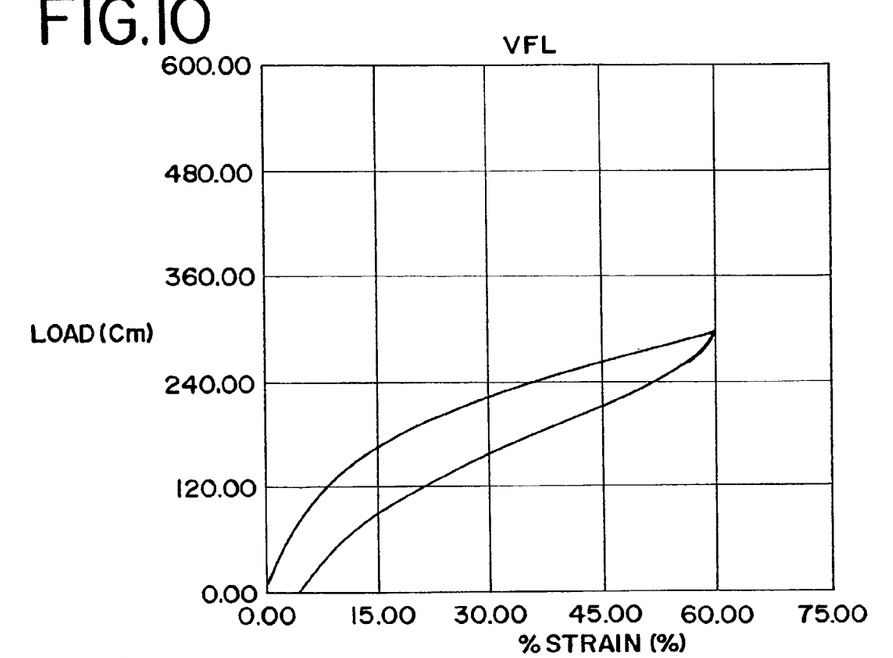
FIG. 10 is a load v. strain graph for an exemplary stretchable material.

The material is a three-ply laminate having inner and outer facing layers of 0.46 ounces per square yard (osy) polypropylene spunbond material (Kimberly-Clark Delta white polypropylene spunbond) and a middle layer of 10 grams per square meter (gsm) Kraton® 666 elastomer strands (3 mm apart) elongated to 4.5 to 5.5 times. The three piece laminate is adhesively laminated with 2.5 gsm Bostik Findley H2096 adhesive. This VFL material was tested as explained below and as shown in FIG. 10.

Example 2

Necked Liner Laminate

Figure 11:
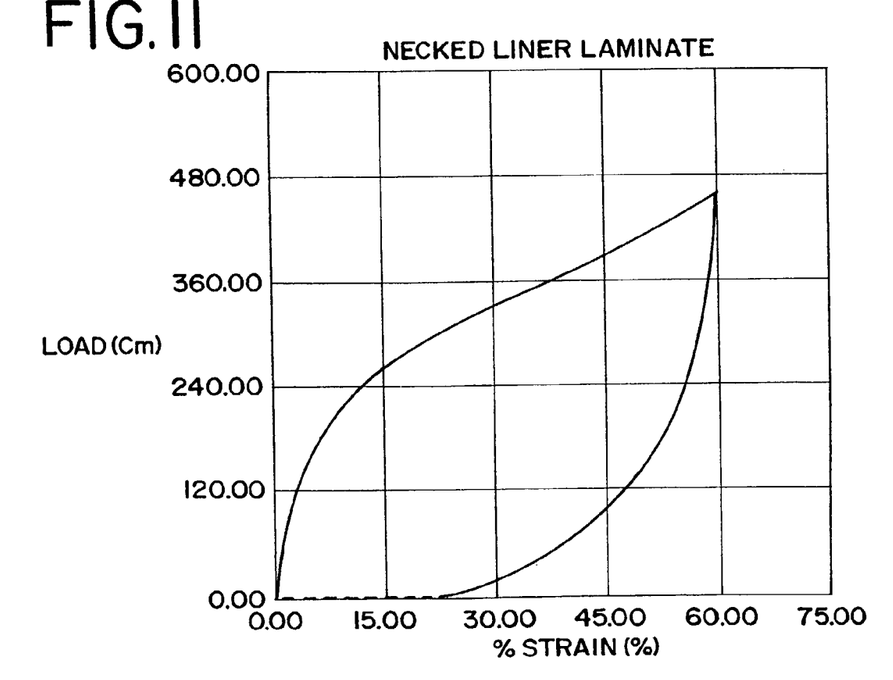
FIG. 11 is a load v. strain graph for a second exemplary stretchable material.

The material is made of a two-ply laminate consisting of a soft co-extruded film laminated to a necked nonwoven material. In particular, the material is made of a layer of 0.4 ounces per square yard (osy) polypropylene spunbond material (Kimberly-Clark Delta white polypropylene spunbond) that was necked 35% (to 65% of initial width) to a final basis weight of 0.6 osy and laminated to a Pliant Film XP-8600 0.7 mil (CaCO3 metallocene Dow Affinity and Dowlex 2035 LLDPE co-extruded film). This material was tested as explained below and as shown in FIG. 11.

Example 3

Necked Liner

The material was made of a nonwoven 0.4 ounces per square yard (osy) polypropylene spunbond material (Kimberly-Clark Delta white polypropylene spunbond) that was necked 65% (to 35% of initial width) to a final basis weight of 0.7 osy.

Figure 12:
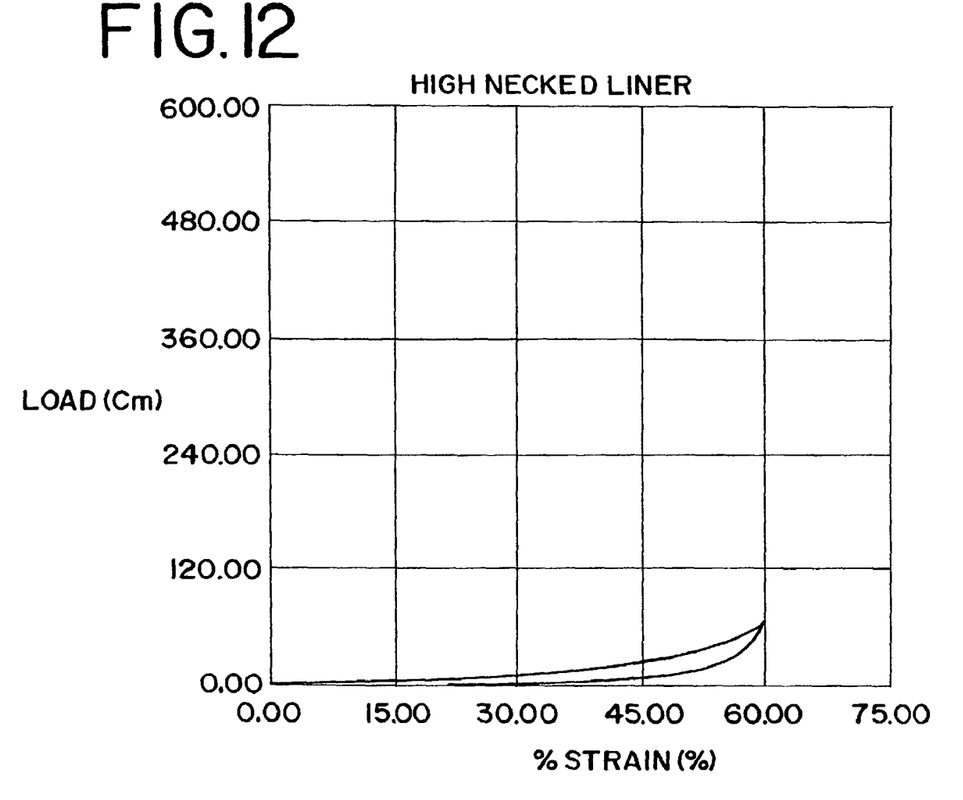
FIG. 12 is a load v. strain graph for an exemplary non-stretchable material.

Referring to FIGS. 10-12, force/strain curves are shown for each of the three exemplary backsheet materials. The stress/strain curves were developed from a test to determine the "stretchability" of "extensibility" of the material, as those terms are defined above. The "Stretchability/Extensibility" test is as follows:

Test Procedure (One-Cycle Tensile Test (without hold time)):
1. A 2 inch wide by 5 inch long specimen was cut from a sheet of sample material. The stretchable direction of the material was in the length direction of the specimen, which is also the test direction.
2. The one-cycle tensile test was conducted on a tensile tester (Model: Synergie 200 available from MTS) located in a room where the temperature was maintained at 23 degrees C and with a relative humidity at 50%.
3. The distance between the lower and upper jaws of the tensile tester were set at 3 inches.
4. The jaws were clamped onto the specimen.
5. The moving (upper) jaw was activated to travel at a constant rate of 5 inches/minute away from the stationary (lower) jaw. The moving jaw was stopped at an extension of 1.8 inches (60% extension).
6. The moving jaw then returned immediately to its initial starting position at a rate of 5 inches/minute.
7. The load v. % strain for the tension and retraction cycle was recorded on a computer equipped with TestWorks Version 3.10 software program available from MTS.

As shown in FIGS. 10 and 11, the VFL and Necked Liner Laminate materials are stretchable as that term is defined above, meaning that they have a hysteresis strain of less than about 28%, or a length of less than about 128% of the original length. As shown in FIG. 12, the Necked Liner material has a hysteresis of greater than about 28%, or a length greater than about 128%, such that it is extensible rather than stretchable as those terms are defined above.

In various constructions, the top sheet 64 can include various woven or nonwoven materials and laminates, which can be stretchable or extensible. In one embodiment, the top sheet 64, shown in FIGS. 2-5 and 7-9, is an extensible material, such as a necked spunbond material. For example, the top-sheet can be composed of a meltblown or spunbonded web of desired fibers, and may also be a bonded-carded web. For example, the topsheet and liner can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8-3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like. In another embodiment, the top sheet can also include an elastic material, such that it is stretchable.

The retention portion 70 is made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 for Absorbent Products Containing Hydrogels With Ability To Swell Against Pressure, U.S. Pat. No. 5,601,542 for Absorbent Composite, and U.S. Pat. No. 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion preferably can be made of a single or dual layer of absorbent material. In one embodiment, the retention portion has an hour-glass shape with enlarged end regions. Alternatively, the retention portion is substantially rectangular. The retention portion can include a folded or multilayered configuration. The retention portion can have a length substantially equal to, or slightly shorter than, the length of the absorbent insert. The retention portion can include one or more barrier layers attached to the absorbent material. In one embodiment, an upper tissue substrate 74 is disposed adjacent the retention portion. Alternatively, a lower tissue substrate 75 can be disposed adjacent an opposite side of the retention portion, or the tissue can completely envelope the retention position.

Referring to FIGS. 6 and 7, the opposite garment side of the end regions of the absorbent insert 50, and in particular, the outer, garment side surface of the back sheet 66, are connected to the bodyside surface of the first and second body panels 4, 6 at attachment locations 88. It should be understood that in an alternative embodiment, the absorbent insert, for example the body side thereof, can be connected to the garment side surface of the first and second body panels. It should be understood that the absorbent insert 50 can be secured using any of the methods of attachment described above, including for example various adhesives, stitching or other bonding methods. The absorbent insert can be secured to the body panels with any configuration of attachment lines, swirls, patterns, spots, etc., or can be a full and continuous attachment therebetween.

In one embodiment, shown in FIG. 3, the absorbent insert 50 is minimally attached to the body panels at an attachment location 90, formed for example along the longitudinally extending centerline 109 thereof. The attachment location 90 can extend along the entire length of the absorbent insert, along only a portion of the length, or at a discrete point, for example proximate midway between the ends 60, 62 of the absorbent insert. In another embodiment (not shown), the attachment location can be formed from a plurality of discrete attachment locations spaced longitudinally along the centerline. In another embodiment (not shown), the entire portion of the absorbent insert overlapping the body panels is attached thereto with a continuous attachment across the width of the absorbent insert, or a portion of the width. In other alternatives, the terminal edges of the absorbent insert 50 can be attached to the body panels, or the absorbent insert can be secured to the body panels along the terminal crotch edges 14, 22 thereof.

In operation, the user applies the undergarment to their body, whether by way of pulling it up around their waist as a pant-like garment or by way of fastening it about their waist with fasteners as a diaper-like garment. As the garment is applied or fitted to the body of the user, the body chassis member 8, 108, and especially the front and rear body panels 4, 6, 104, 106, are elongated from a first condition, preferably relaxed, to a second condition, preferably elongated, in at least one direction, preferably the lateral direction 502. Of course, the body chassis member 8, 108 can also elongate in the longitudinal direction 500 from the crotch to the waist. In one embodiment, the body chassis member 8, 108, and in particular one or the other of the body panels 4, 6, 104, 106, is elongated in a lateral direction between about 20% and about 300%, in another embodiment between about 50% and about 200%, and in another embodiment between about 100% and about 150%, as it is applied to the user. The body chassis member 8, 108 is elongated by virtue of a tensile force being applied thereto as the body chassis member conforms to the body of the user.

As the body chassis member 8, 108 is elongated, with the attendant application of a tensile force, the absorbent insert, which includes in one embodiment an extensible top sheet 64 and a stretchable/elastic back sheet 66, stretches or elongates with the body panels. The back sheet can be elongated in one embodiment between about 20% and about 150%, in another embodiment between about 40% and about 125% and in another embodiment between about 50% and about 100%. Since the retention portion 70 is free floating, or alternatively is minimally attached to the stretchable top sheet and the stretchable/elastic back sheet, e.g., along the longitudinal center line 108, the retention portion 70 does not restrict the elongation of the back sheet 66 and top sheet 64, or the attached body panels 4, 6.

In another aspect, the manufacturer or retailer of the aforedescribed absorbent garments provides instructional information to the user, for example by way of textual or pictorial indicia on the packaging materials, about how the garment works. For example, the manufacturer or retailer can explain to the end user the advantages of the stretchable/elastic absorbent insert, and the resultant ability of the body panels to freely conform to the body of the user without restriction from the retention portion, thereby improving the conformance and fit of the garment.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A disposable undergarment comprising:
   a body panel comprising a body side surface and a garment side surface; and an absorbent insert comprising a back sheet connected to a top sheet and a retention portion disposed between said back sheet and said top sheet, wherein said back sheet and top sheet are formed separately from said body panel and do not form any portion thereof, wherein at least one of said back sheet and said top sheet is stretchable and comprises an elastic material, and wherein at least one of said back sheet and said top sheet is connected to one of said body side surface and said garment side surface of said body panel, wherein said retention portion is minimally attached to at least one of said back sheet and said top sheet along a longitudinally extending centerline of said retention portion, with portions of said retention portion overlapping said at least one of said back sheet and said top sheet on either side of said longitudinally extending attachment along the centerline of said retention portion being free of any attachment to either of said back sheet or said top sheet.

2. The disposable undergarment of claim 1 wherein said back sheet is stretchable and comprises said elastic material.

3. The disposable undergarment of claim 2 wherein said elastic material comprises an elastic film.

4. The disposable undergarment of claim 2 wherein said back sheet comprises a laminate comprising a non-woven material and said elastic material.

5. The disposable undergarment of claim 1 wherein said body panel comprises a front body panel comprising a terminal waist edge and a terminal crotch edge and a rear body panel comprising a terminal waist edge and a terminal crotch edge, wherein said front and rear body panels are formed separately with said terminal crotch edges of each of said front and rear body panels extending laterally across at least a longitudinal centerline of said front and rear body panels, and wherein said terminal crotch edge of said rear body panel is longitudinally spaced from and forms a gap with said terminal crotch edge of said front body panel, and wherein said absorbent insert bridges said gap and is connected to said front and rear body panels.

6. The disposable undergarment of claim 1 wherein said body panel comprises an elastic material.

7. The disposable undergarment of claim 6 wherein said body panel comprises a laminate comprising a non-woven material outer layer, an elastic core comprising said elastic material and a non-woven material inner layer.

8. The disposable undergarment of claim 1 wherein said absorbent insert is connected to said body panel at an attachment location positioned along at least a longitudinally extending centerline of said absorbent insert.

9. The disposable undergarment of claim 1 wherein said absorbent insert is secured to a bodyside surface of said body panel.

10. The disposable undergarment of claim 1 wherein said retention portion is directly minimally attached to said at least one of said back sheet and said top sheet along said longitudinally extending centerline.

11. The disposable undergarment of claim 10 wherein said retention portion comprises an absorbent material and a tissue substrate.

12. The disposable undergarment of claim 1 wherein said body panel comprises front and rear terminal waist edges.

13. A disposable undergarment comprising:
a stretchable body panel, wherein said body panel comprises a front body panel comprising a terminal waist edge and a terminal crotch edge and a rear body panel comprising a terminal waist edge and a terminal crotch edge, wherein said front and rear body panels are formed separately with said terminal crotch edges of each of said front and rear body panels extending laterally across at least a longitudinal centerline of said front and rear body panels, and wherein said terminal crotch edge of said rear body panel is longitudinally spaced from and forms a gap with said terminal crotch edge of said front body panel, and wherein said absorbent insert bridges said gap and is connected to said front and rear body panels; and
an absorbent insert comprising a back sheet connected to a top sheet and a retention portion disposed between said back sheet and said top sheet, wherein said back sheet is stretchable and comprises an elastic material, and wherein a garment side surface of said back sheet is connected to a body side surface of said front body panel.

14. The disposable undergarment of claim 13 wherein said elastic material comprises an elastic film.

15. The disposable undergarment of claim 14 wherein said back sheet comprises a laminate comprising a non-woven material and said elastic material.

16. The disposable undergarment of claim 13 wherein said retention portion is minimally attached to at least one of said back sheet and said top sheet along a longitudinally extending centerline of said retention portion, with portions of said retention portion overlapping said at least one of said back sheet and said top sheet on either side of said longitudinally extending attachment along the centerline of said retention portion being free of any attachment to either of said back sheet or said top sheet.

17. The disposable undergarment of claim 13 wherein said body panel comprises an elastic material.

18. The disposable undergarment of claim 17 wherein said body panel comprises a laminate comprising a non-woven material outer layer, an elastic core comprising said elastic material and a non-woven material inner layer.

19. The disposable undergarment of claim 13 wherein said absorbent insert is connected to said body panel at an attachment location positioned along at least a longitudinally extending centerline of said absorbent insert.

* * * * *